(12) United States Patent
Miyama

(10) Patent No.: US 10,198,593 B2
(45) Date of Patent: Feb. 5, 2019

(54) INFORMATION PROCESSING APPARATUS, INFORMATION PROCESSING METHOD AND PROGRAM

(71) Applicant: SONY CORPORATION, Tokyo (JP)

(72) Inventor: Seiji Miyama, Kanagawa (JP)

(73) Assignee: Sony Corporation, Tokyo (JP)

( * ) Notice: Subject to any disclaimer, the term of this patent is extended or adjusted under 35 U.S.C. 154(b) by 143 days.

(21) Appl. No.: 14/357,458

(22) PCT Filed: Oct. 18, 2012

(86) PCT No.: PCT/JP2012/006662
§ 371 (c)(1),
(2) Date: May 9, 2014

(87) PCT Pub. No.: WO2013/073105
PCT Pub. Date: May 23, 2013

(65) Prior Publication Data
US 2014/0317143 A1    Oct. 23, 2014

(30) Foreign Application Priority Data

Nov. 18, 2011 (JP) ................. 2011-252644

(51) Int. Cl.
G06F 17/30        (2006.01)
G06F 21/62        (2013.01)
(Continued)

(52) U.S. Cl.
CPC .......... *G06F 21/6245* (2013.01); *G06F 19/00* (2013.01); *G06F 19/321* (2013.01); *G06F 19/3418* (2013.01); *G16H 40/20* (2018.01)

(58) Field of Classification Search
CPC ........ G06F 17/30017; G06F 17/30265; G06F 17/3028; G06F 19/321; G06F 17/241;
(Continued)

(56) References Cited

U.S. PATENT DOCUMENTS 6,638,223 B2 * 10/2003 Lifshitz .................... A61B 5/00
                                                   600/437
6,938,029 B1 * 8/2005 Tien .................. G06F 17/30017
(Continued)

FOREIGN PATENT DOCUMENTS

CN    201708827 U    1/2011
CN    102231172 A    11/2011
(Continued)

OTHER PUBLICATIONS

Japanese Office Action dated Nov. 24, 2015, for corresponding Japanese Appln. No. 2011-252644 (7 pages).
(Continued)

*Primary Examiner* — Dennis Truong
(74) *Attorney, Agent, or Firm* — K&L Gates LLP

(57) ABSTRACT

A medical information server is provided. The medical information server includes a medical information unit configured to determine a diagnose authority to an information terminal thereby allowing a diagnosis by the information terminal to be identified by the diagnose authority. An information terminal and a diagnostic information processing system are also provided.

12 Claims, 10 Drawing Sheets

(51) Int. Cl.
*G06F 19/00* (2018.01)
*G16H 40/20* (2018.01)

(58) Field of Classification Search
CPC ............ G06F 3/04842; G06F 19/3418; G06F 19/3481; G06F 2221/2149; G06F 2221/2141; G06F 19/324; G06F 19/325; G06F 21/00; G06F 21/31; A61B 2560/0295; A61B 5/00; A61B 5/4824; A61B 5/7435; A61B 5/748; A61B 6/00; A61B 6/465; A61B 8/00; A61B 8/465; A61B 5/0013; G06T 19/00; G06T 2210/41; G06T 2219/004; Y10S 707/99931; G06Q 2220/10; G16H 15/00; G16H 50/20; G16H 80/00; H04N 2201/0079; H04L 2209/88
USPC .......... 707/E17.009, E17.031, 783; 345/634; 600/440; 700/17, 18, 83; 715/230; 705/3, 51; 726/28, 29
See application file for complete search history.

(56) References Cited

U.S. PATENT DOCUMENTS

| | | | | | |
|---|---|---|---|---|---|
| 7,003,349 | B1* | 2/2006 | Andersson | ......... | A61N 1/37247 600/510 |
| 7,218,722 | B1* | 5/2007 | Turner | ................... | H04L 12/66 370/352 |
| 7,453,472 | B2* | 11/2008 | Goede | ................... | G06F 17/241 345/634 |
| 7,490,048 | B2* | 2/2009 | Joao | ..................... | G06F 19/322 705/2 |
| 9,656,092 | B2* | 5/2017 | Golden | ................ | A61B 5/7465 |
| 9,800,464 | B2* | 10/2017 | McEntee | ............ | H04L 41/0813 |
| 2001/0031071 | A1* | 10/2001 | Nichols | ................ | A61B 5/1171 382/115 |
| 2002/0019751 | A1* | 2/2002 | Rothschild | ............ | G06F 19/321 705/3 |
| 2002/0164059 | A1* | 11/2002 | DiFilippo | ............. | G06T 7/0012 382/128 |
| 2006/0155583 | A1* | 7/2006 | Teshima | ................ | G06F 19/321 705/3 |
| 2007/0050213 | A1* | 3/2007 | Matsushima | ........... | G06F 19/00 705/3 |
| 2007/0106633 | A1* | 5/2007 | Reiner | .................. | G06F 19/321 |
| 2007/0232885 | A1* | 10/2007 | Cook | .................... | G06F 19/321 600/407 |
| 2007/0234219 | A1* | 10/2007 | Bhattaru | ............. | G06F 19/3406 715/744 |
| 2008/0184330 | A1* | 7/2008 | Lal | .......................... | G06F 21/31 726/1 |
| 2009/0073493 | A1* | 3/2009 | Kuramochi | ........... | G06F 21/608 358/1.16 |
| 2010/0017225 | A1* | 1/2010 | Oakley | ................. | G06F 19/322 705/2 |
| 2010/0179831 | A1* | 7/2010 | Brown | .................. | G06F 19/322 705/3 |
| 2011/0113065 | A1* | 5/2011 | Cupka | ............... | G06F 17/30168 707/783 |
| 2011/0173308 | A1* | 7/2011 | Gutekunst | ........... | G06F 19/3406 709/222 |
| 2011/0199390 | A1* | 8/2011 | Iizuka | ................... | G06F 19/321 345/629 |
| 2011/0301441 | A1* | 12/2011 | Bandic | ................. | A61B 5/0059 600/306 |
| 2012/0159391 | A1* | 6/2012 | Berry | ................... | A61B 5/4824 715/823 |
| 2012/0227113 | A1* | 9/2012 | Wise | ..................... | G06F 19/321 726/29 |
| 2013/0024382 | A1* | 1/2013 | Dala | .................... | G06F 21/602 705/51 |
| 2013/0174273 | A1* | 7/2013 | Grab | ...................... | G06F 21/00 726/28 |
| 2015/0347682 | A1* | 12/2015 | Chen | .................... | G06F 19/321 705/2 |

FOREIGN PATENT DOCUMENTS

| | | |
|---|---|---|
| JP | 2003-303237 | 10/2003 |
| JP | 2009-060945 | 3/2009 |
| JP | 2009-230304 | 6/2010 |
| JP | 2010-134540 | 6/2010 |

OTHER PUBLICATIONS

Chinese Office Action dated May 6, 2016 for corresponding Chinese Appln. No. 201280054876.3 (18 pages).

\* cited by examiner

| Terminal ID | Doctor ID | Terminal nickname | Size of screen | Screen resolution | Input apparatus | Diagnostic confirmation/temporal confirmation flag |
|---|---|---|---|---|---|---|
| 1 | 3 | 5C | 13.1 | 1920x1200 | Keyboard, mouse | 1 |
| 2 | 5 | 5A | 3.5 | 960x640 | Touch panel | 0 |

| Terminal ID | Doctor ID | Image ID | Position coordinate | Magnification | Time and date |
|---|---|---|---|---|---|
| 1 | 1 | 34 | (x1, y1, z1) | 20 | 2011/07/01 09:23 |
| 1 | 1 | 34 | (x2, y2, z2) | 40 | 2011/07/01 09:39 |
| 1 | 1 | 34 | (x3, y3, z3) | 40 | 2011/07/01 09:51 |
| 1 | 1 | 34 | (x4, y4, z4) | 40 | 2011/07/01 10:02 |

| Diagnosis information ID | Terminal ID | Doctor ID | Image ID | x coordinate | y coordinate | z coordinate | Magnification | Diagnosis /finding | Diagnosis confirmation |
|---|---|---|---|---|---|---|---|---|---|
| 1 | 1 | 3 | 34 | 1230 | 23412 | 23 | 20 | Indication of X | 1 |
| 2 | 3 | 1 | 2234 | 87123 | 7123 | 3 | 40 | Suspicion of Y | 0 |

INFORMATION PROCESSING APPARATUS, INFORMATION PROCESSING METHOD AND PROGRAM

CROSS REFERENCES TO RELATED APPLICATIONS

The present application is a national stage of International Application No. PCT/JP2012/006662 filed on Oct. 18, 2012 and claims priority to Japanese Patent Application No. 2011-252644 filed on Nov. 18, 2011, the disclosure of which is incorporated herein by reference.

BACKGROUND

The present disclosure relates to an information processing apparatus, an information processing method and a program that store image data obtained by a microscope and supply the stored image data to an information terminal in a field of medicine, pathology, biology, material, or the like.

A remote diagnostic information processing system in which information processing apparatuses placed at a plurality of medical facilities are connected each other through a network such as the Internet and these information processing apparatuses are each connected to a data center through the network has been known (see, for example, Patent Literature 1). In this remote diagnostic information processing system, it is possible to issue a diagnosis request for an inspection image to an information processing apparatus placed at a medical facility (diagnosis side) from an information processing apparatus placed at another medical facility (requestor) through a data center. When the data center receives the diagnosis request for the inspection image from the information processing apparatus (requestor), it confirms if the information processing apparatus (diagnosis side) has a display capability suited to a diagnostic purpose and sends the inspection image as a diagnosis target to this information processing apparatus.

CITATION LIST

Patent Literature

PTL 1: Japanese Patent Application Laid-open No. 2003-303237

SUMMARY

Incidentally, in recent years, performance of a portable information terminal has been significantly improved and performing a diagnosis of an inspection image displayed on the portable information terminal has been considered. However, in this type of portable information terminal, although an improvement of portability by reduction in size and weight is very important, a display capability such as screen resolution or color resolution is limited. Since a diagnosis of an inspection image is performed by visual inspection using a shape, color, or the like of the image as a guide, the accuracy of a diagnosis of an inspection image displayed on a portable information terminal with a low display capability may be limited.

In view of the circumstances as described above, there is a need for an information processing apparatus, an information processing method and a program that allow an improvement of reliability of a diagnosis of an inspection medical image.

In an embodiment, a medical information server is provided. The medical information server includes a medical information unit configured to determine a diagnose authority to an information terminal thereby allowing a diagnosis by the information terminal to be identified by the diagnose authority.

In another embodiment, an information terminal is provided. The information terminal includes an information terminal unit configured to provide information that allows a determination of a diagnose authority thereby allowing a diagnosis by the information terminal to be identified by the diagnose authority.

In yet another embodiment, a diagnostic information processing system is provided. The diagnostic processing system includes a medical information server comprising a medical server unit configured to determine a diagnose authority; and an information terminal comprising an information terminal unit configured to provide information to the server, wherein the diagnose authority is determined to the information terminal based on the information thereby allowing a diagnosis by the information terminal to be identified by the diagnose authority.

An information processing apparatus according to an embodiment of the present disclosure includes a terminal information management section, an image providing section and a diagnostic information management section.

The terminal information management section is configured to manage information on an authority to diagnose each medical image of a plurality of information terminals.

The image providing section is configured to return a corresponding medical image, in response to a request for browsing the medical image from any one of the plurality of information terminals, to the information terminal.

The diagnostic information management section is configured to differentiate and manage a diagnostic result obtained from the information terminal with respect to the medical image provided to the information terminal based on information on an authority to diagnose of the information terminal.

The diagnostic information management section may differentiate and manage a diagnostic result provided from a first information terminal that is an information terminal being granted an authority to diagnose a medical image as a first confirmed diagnostic result, and a diagnostic result provided from a second information terminal that is an information terminal not being granted the authority to diagnose the medical image as a second confirmed diagnostic result.

The diagnostic information management section may return the second confirmed diagnostic result and a diagnosis target image corresponding to the second confirmed diagnostic result in response to a demand from the first information terminal.

The information processing apparatus may further include a browsing history management section configured to manage browsing history of the medical image of each of the plurality of information terminals and return the browsing history in response to a request from the information terminal.

The terminal information management section may set an authority to diagnose the medical image of the information terminal based on a specification of a user interface of the information terminal.

An information processing method according to another embodiment of the present disclosure includes: managing, by a terminal information management section, information on an authority to diagnose each medical image of a plurality of information terminals; returning, by an image providing section, a corresponding medical image, in response to a request for browsing the medical image from any one of the plurality of information terminals, to the information terminal; and differentiating and managing, by a diagnostic information management section, a diagnostic result obtained from the information terminal with respect to the medical image provided to the information terminal based on information on an authority to diagnose of the information terminal.

A program according to another embodiment of the present disclosure causes a computer to function as: a terminal information management section configured to manage information on an authority to diagnose each medical image of a plurality of information terminals; an image providing section configured to return a corresponding medical image, in response to a request for browsing the medical image from any one of the plurality of information terminals, to the information terminal; and a diagnostic information management section configured to differentiate and manage a diagnostic result obtained from the information terminal with respect to the medical image provided to the information terminal based on information on an authority to diagnose of the information terminal.

As described above, according to the embodiments of the present disclosure, it is possible to perform a diagnosis efficiently and improve the accuracy of a diagnosis.

Additional features and advantages are described herein, and will be apparent from the following Detailed Description and the figures.

BRIEF DESCRIPTION OF THE FIGURES

FIG. 7 is a diagram showing a second information terminal that is displaying a medical image and the like.

FIG. 8 is a diagram showing the first information terminal that is displaying a medical image and the like.

FIG. 9 is another diagram showing the first information terminal that is displaying a medical image and the like.

FIG. 12 is a diagram showing an example of a terminal information table created by a terminal information management section of the medical information server apparatus shown in FIG. 1.

FIG. 13 is a diagram showing an example of a browsing history table created by a browsing history management section of the medical information server apparatus shown in FIG. 1.

FIG. 14 is a diagram showing an example of a diagnostic information table created by a diagnostic information management section of the medical information server apparatus shown in FIG. 1.

DETAILED DESCRIPTION

Figure 1:
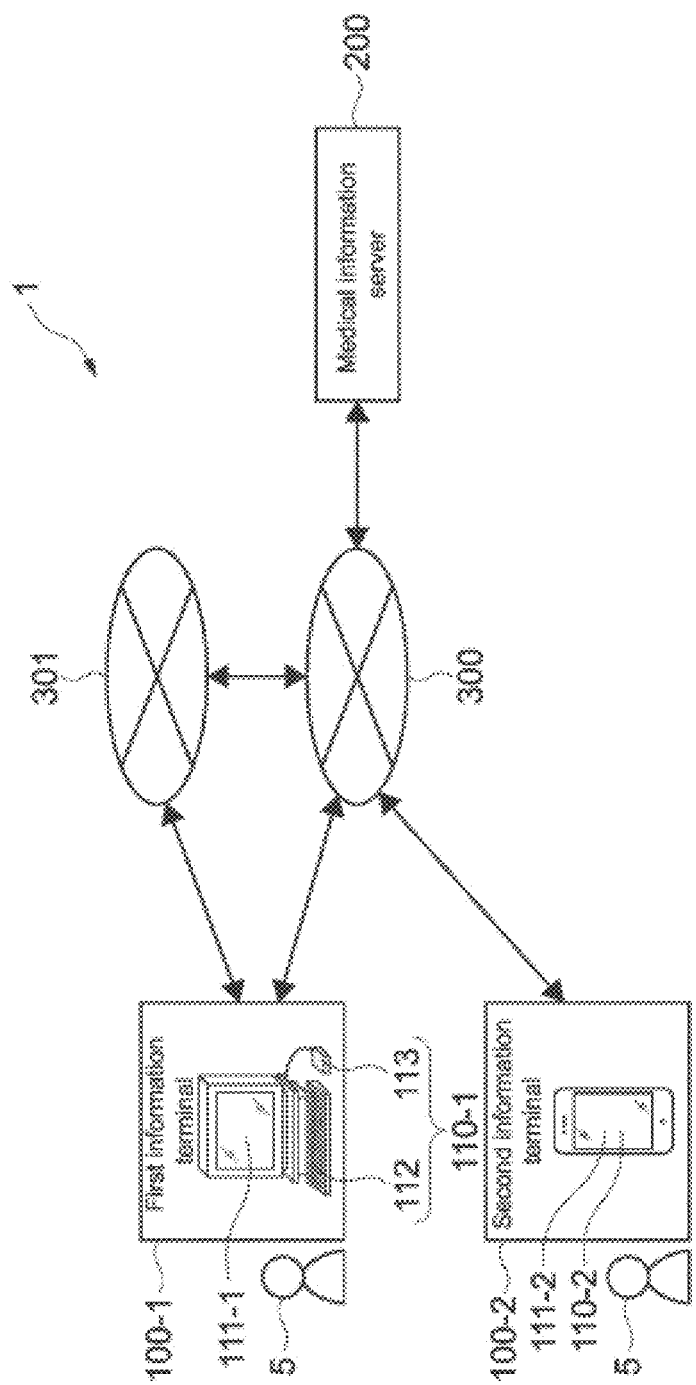
FIG. 1 is a diagram showing an information processing system according to an embodiment of the present disclosure.

Hereinafter, an embodiment of the present disclosure will be described with reference to the drawings.

(Overview of the Embodiment)

The embodiment relates to an information processing system that efficiently performs a diagnosis of an inspection medical image such as an image taken by a microscope using a plurality of information apparatuses.

The information processing system according to the embodiment includes a server apparatus and a plurality of information terminals which are connected to the server apparatus through a network and are capable of diagnosing an inspection medical image stored in the server apparatus.

In the embodiment, two types or more of information terminals that have different specifications of user interfaces such as a screen size, screen resolution and color resolution of a display apparatus of an information terminal and a type of an input apparatus (pointing device) are assumed as the plurality of information terminals. Here, for example, an information terminal with a relatively high specification of a user interface, such as an information terminal which has a relatively large screen, relatively high screen resolution and relatively high color resolution of a display apparatus, or, an information terminal which has a relatively high accuracy of pointing of an input apparatus, is referred to as "a first information terminal". An information terminal with a lower specification of a user interface than the first information terminal is referred to as "a second information terminal". Specifically, a desktop personal computer may be used as the first information terminal. As the second information terminal, for example, a cellular phone, smartphone, laptop personal computer, or tablet terminal may be used. It should be noted that, in the present disclosure, since there is no absolute standard of a user interface for sorting the first information terminal and the second information terminal, they may be changed as appropriate.

In recent years, a CPU (Central Processing Unit) speed of an information terminal focusing on portability has been increasing and an image drawing capability of the information terminal has also been improved. Further, it has been become possible to deal with a large image such as an inspection medical image. However, in a case where a screen size, screen resolution and color resolution of a display section are small, this brings disadvantages when finding a target part in an image because an actual diagnosis of an inspection medical image is performed mainly by visual inspection. Moreover, for example, although a mouse or touch panel is generally used as a type of an input section (pointing device), there is a difference in pointing accuracy of coordinates between them. When the pointing accuracy is insufficient, it becomes difficult to select the position with high accuracy even if a target part can be found in an image.

Accordingly, it may cause a reduction in the transmission accuracy of a diagnostic result.

In this regard, in the information processing system according to the embodiment, a server apparatus differentiates and manages diagnostic results of the first information terminal and the second information terminal based on the authority to diagnose granted to each of the information terminals. The server apparatus manages a diagnostic result obtained by the second information terminal as a tentative diagnostic information which is not confirmed formally and manages a diagnostic result obtained by the first information terminal as a diagnostic information which is confirmed formally. It thus becomes possible to perform, for example, a formal diagnosis by the first information terminal again as for the unconfirmed diagnostic result obtained by the second information terminal. In such a method, both the first information terminal and the second information terminal can be used for a diagnosis, thereby enabling the diagnosis to be performed more frequently and improving the quality of the diagnosis because it is difficult to obtain a formal diagnostic result by the second information terminal.

In the following, an information processing apparatus and an information terminal according to the embodiment of the present disclosure will be described in detail.

(Configuration of Information Processing System)

FIG. 1 is a diagram showing an information processing system according to the embodiment of the present disclosure.

As shown in FIG. 1, an information processing system 1 includes a medical information server apparatus 200 which is an information processing apparatus, a first information terminal 100-1, and a second information terminal 100-2. The medical information server apparatus 200, the first information terminal 100-1, and the second information terminal 100-2 can be connected so as to be able to communicate with one another through a network 300. The first information terminal 100-1 may be an information terminal such as a desktop information terminal placed in a hospital area, for example. The second information terminal 100-2 may be, for example, an information terminal designed focusing on portability, which is used by connecting to the network 300 directly in the hospital area, or by connecting to the network 300 of the information processing system 1 through an external network 301 from outside the hospital area. The information system 1 may include two or more information terminals.

Figure 2:
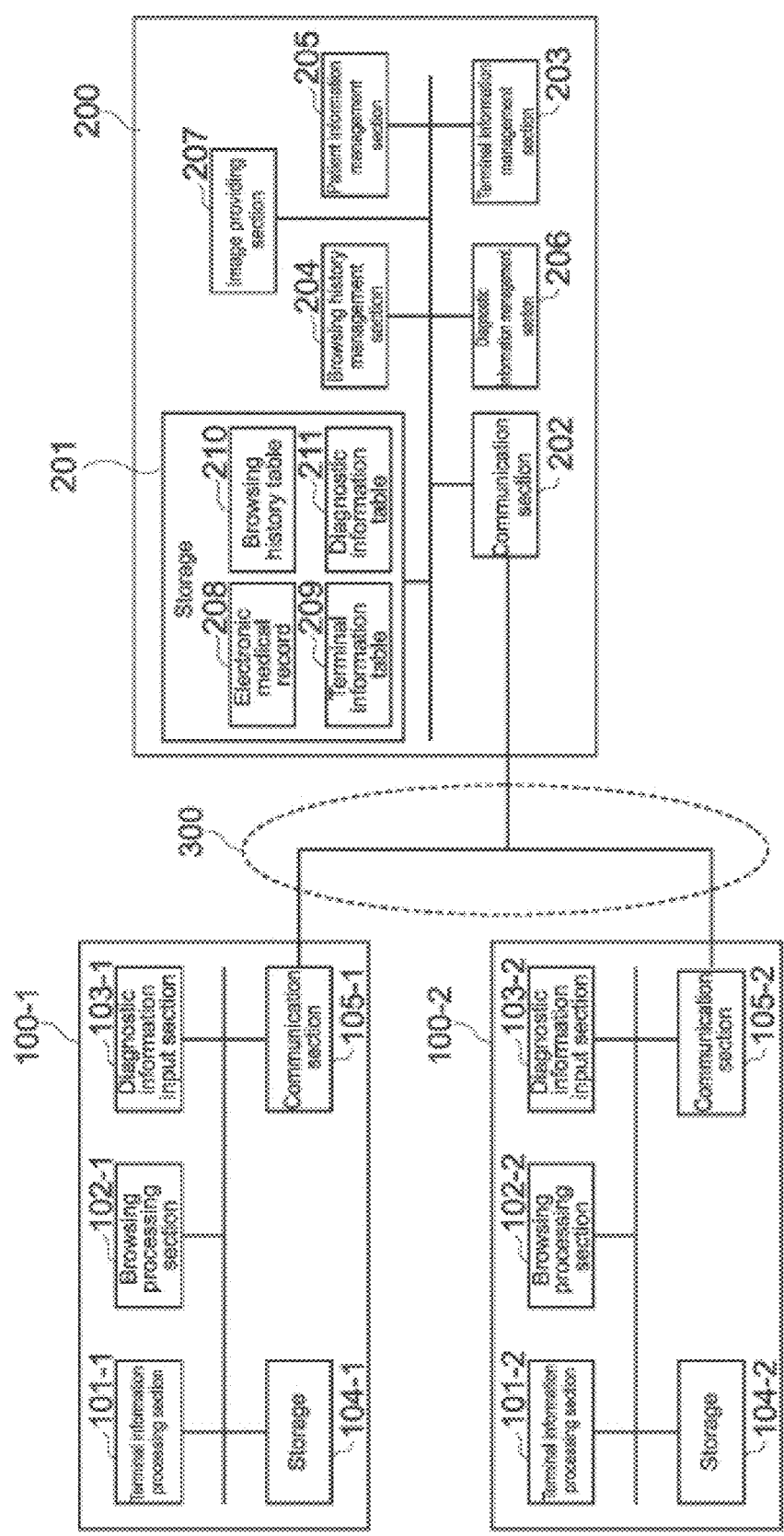
FIG. 2 is a block diagram showing a software configuration of the information processing system shown in FIG. 1.

FIG. 2 is a block diagram showing a configuration of the medical information server apparatus 200, the first information terminal 100-1 and the second information terminal 100-2 in the information processing system 1 shown in FIG. 1.

(Configuration of Information Terminal)

Since the functional configurations of the first information terminal 100-1 and the second information terminal 100-2 are similar, the configuration will be described by collectively referring to these terminals as "an information terminal 100".

The information terminal 100 is provided with a terminal information processing section 101 (101-1, 101-2), a browsing processing section 102 (102-1, 102-2), a diagnostic information input section 103 (103-1, 103-2), storage 104 (104-1, 104-2), and a communication section 105 (105-1, 105-2).

In the storage 104, not only information such as a terminal ID, a nickname, user interface specification information (e.g., the screen size and the screen resolution of the display section, and the type of the input section) but also a doctor ID which is assigned in advance to a doctor who is a user 5 of the information terminal 100 is stored as information related to the information terminal 100.

The terminal information processing section 101 reads out information related to an information terminal stored in the storage 104 in response to a request from the medical information server apparatus 200 and responds to the medical information server apparatus 200 via the communication section 105.

The browsing processing section 102 performs processing for displaying a GUI (Graphical User Interface) for operating an information terminal and for acquiring a medical image, diagnostic information, and the like from the medical information server apparatus 200 and displaying them so as to enable a doctor to browse them.

The diagnostic information input section 103 performs processing of an input such as a diagnostic result for a browsed medical image by a doctor.

The communication section 105 performs processing of communication with the medical information server apparatus 200 through the networks 300 and 301.

(Functional Configuration of Medical Information Server Apparatus 200)

As shown in FIG. 2, the medical information server apparatus 200 includes storage 201, a communication section 202, a terminal information management section 203, a browsing history management section 204, a patient information management section 205, a diagnostic information management section 206, and an image providing section 207.

The storage 201 stores an electronic medical record 208, a terminal information table 209, a browsing history table 210, a diagnostic information table 211, and the like. In the electronic medical record 208, patient information including a medical image is recorded. In the terminal information table 209, information related to the information terminal 100 is registered. In the browsing history table 210, browsing history for each of the information terminals 100 is registered. In the diagnostic information table 211, diagnostic information is registered.

The communication section 202 performs processing of communication with the information terminal 100 through the networks 300 and 301.

The terminal information management section 203 manages information related to the information terminal 100 by using the terminal information table 209.

FIG. 12 is a diagram showing a configuration of the terminal information table 209.

In the terminal information table 209, a terminal ID, a doctor ID, a nickname, user interface specification information, and a diagnostic confirmation/temporal confirmation flag are registered as information related to the information terminal.

The terminal ID is an ID assigned uniquely to each of the information terminals 100.

The doctor ID is an ID assigned uniquely to a doctor who is a user 5 of the information terminal 100.

The nickname is a name of the information terminal 100 arbitrarily set by the user 5.

The user interface specification information is configured by information related specifications of the user interfaces such as the display section and the input section. In this example, the screen size and the screen resolution of the display section in the information terminal 100, the type of the input section (pointing device) in the information terminal 100, and the like, are employed as the user interface specification information.

The diagnostic confirmation/temporal confirmation flag is a flag for setting an authority to diagnose which is granted to the information terminal 100. The authority to diagnose includes "diagnostic confirmation" and "temporal diagnostic confirmation". In the diagnostic confirmation, a diagnostic result can be confirmed. In the temporal diagnostic confirmation, a diagnostic result can be temporally confirmed, although the diagnostic result may not be confirmed. In FIG. 12, in a case where an authority of "diagnostic confirmation" is granted, "1" is set as the diagnostic confirmation/temporal confirmation flag and in a case where an authority of "temporal diagnostic confirmation" is granted, "0" is set as the diagnostic confirmation/temporal confirmation flag. Which authority is granted to the information terminal 100 depends on the user interface specification information of the information terminal 100, basically.

In this example, since the first information terminal 100-1 is assumed to be a terminal with relatively high user interface specifications and the second information terminal 100-2 is assumed to be a terminal with relatively low user interface specifications, the authority of "diagnostic confirmation" is granted to the first information terminal 100-1 and the authority of "temporal diagnostic confirmation" is granted to the second information terminal 100-2.

Now, return to the description of FIG. 2. In the patient information management section 205, patent information including a medical image is managed. The patent information including a medical image is configured by a patient ID, a patient name, a gender, a date of birth, an ID of a medical image, and the like. The patient information management section 205 takes out the corresponding medical image from the storage 201 in response to a browsing request for a medical image acquired from the information terminal 100 via the communication section 202 and responds to the information terminal 100 as a request source.

The browsing history management section 204 manages browsing history of a medical image for each combination of the information terminal 100 and the user 5 by using the browsing history table 210.

The browsing history table 210 is a table in which information such as position information, a magnification, and a time and date of a browsed area in a whole space of a medical image is registered as browsing history information for each combination of the information terminal 100 and the user 5.

FIG. 13 is a diagram showing a configuration of the browsing history table 210.

In the browsing history table 210, a terminal ID, a doctor ID, an image ID, position coordinates, a magnification, and a time and date are registered.

The image ID is an ID which is assigned uniquely to a medical image.

The position coordinates are central position coordinates (xyz coordinates) of the browsed area in a whole space of a medical image.

The magnification is a zoom magnification during browsing.

The time and date is a browsing time and date when the browsing started.

The browsing history table 210 composed as described above can be used as information for reproducing that which user 5 browsed which area of which medical image in which order on which information terminal 100.

Now, return to the description of FIG. 2. The diagnostic information management section 206 manages diagnostic information acquired from the information terminal 100 by using the diagnostic information table 211.

FIG. 14 is a diagram showing a configuration of the diagnostic information table 211.

In the diagnostic information table 211, a diagnostic information ID, a terminal ID, a doctor ID, an image ID, position coordinates, a magnification, a diagnosis/finding, and information as to existence or non-existence of diagnostic confirmation. It should be noted that a z coordinate of the position coordinates is information for specifying a focal position in a case where one medical image is configured by a plurality of images each having a different focal point.

The diagnostic information ID, the terminal ID, the doctor ID, the image ID, the position coordinates, and the magnification are the same as those registered in the terminal information table 209 or the browsing history table 210.

The diagnosis/finding is a diagnostic result input by a doctor who is a user 5 through an observation of the medical image.

The information as to existence or non-existence of diagnostic confirmation is information showing existence or non-existence of an authority to confirm a diagnosis granted to the information terminal 100 which is a provider of the diagnostic information.

With respect to a browsing request for a medical image from the information terminal 100, or the like, the image providing section 207 returns the medical image to the information terminal 100.

(Medical Information Server Apparatus 200, Hardware Configuration of Information Terminal 100)

The medical information server apparatus 200 is configured by using typical computer hardware.

Figure 3:
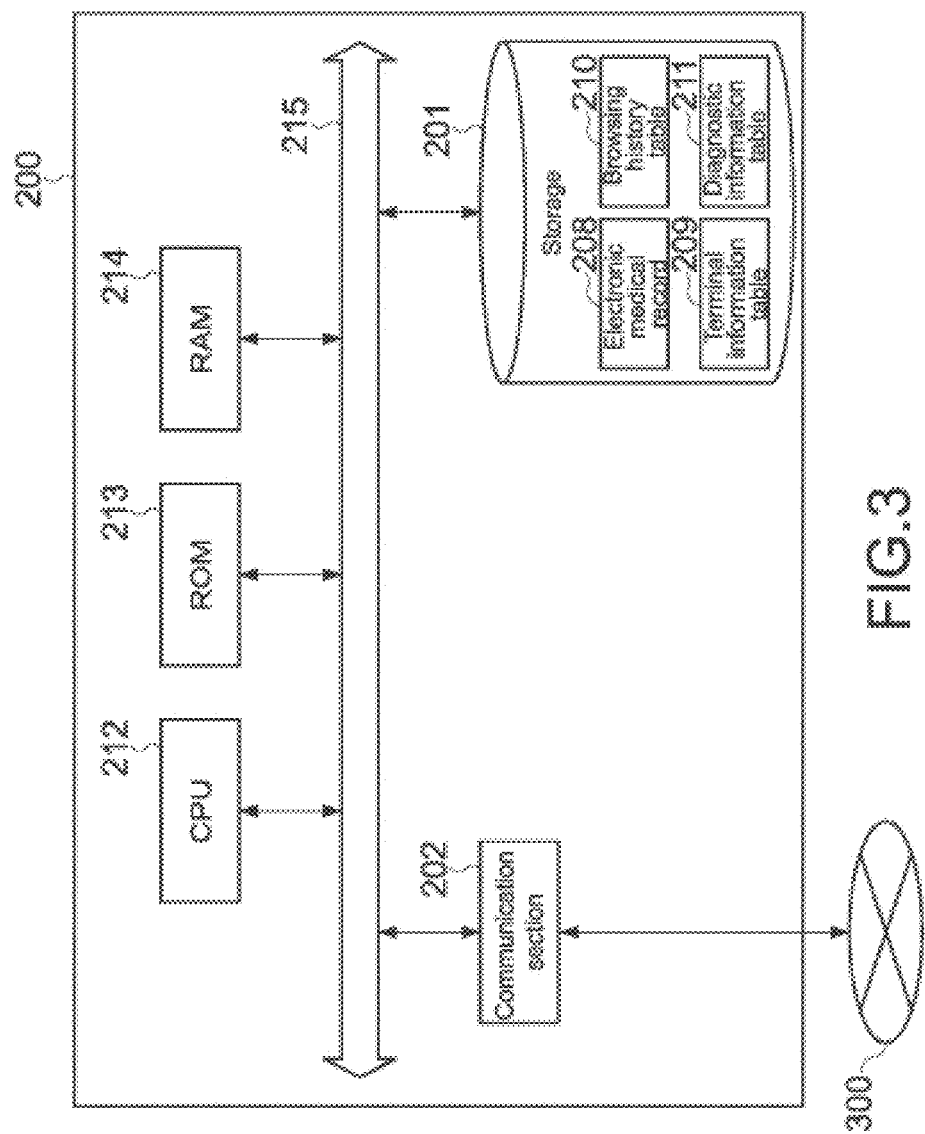
FIG. 3 is a block diagram showing a hardware configuration of a medical information server apparatus configuring the information processing system shown in FIG. 1.

FIG. 3 is a diagram showing a hardware configuration of the medical information server apparatus 200.

The medical information server apparatus 200 includes a system bus 215, a CPU 212, a ROM (Read-Only Memory) 213, a RAM (Random Access Memory) 214, a communication section 202, and storage 201. These are connected with one another via the system bus 215. Although the medical information server apparatus 200 also includes an input section and a display section that are user interfaces, these are omitted in FIG. 3.

In the ROM 213 or storage 201, a program for software processing which the medical information server apparatus 200 should execute, and the like are stored. The CPU 212 loads an appropriate program from the ROM 213 or the storage 201 into the RAM 214 and performs calculation processing for an interpretation and execution in order to execute software processing which the medical information server apparatus 200 should execute. Accordingly, the CPU 212 causes a computer to function as the terminal information management section 203, the browsing history management section 204, the patient information management section 205, and the diagnostic information management section 206.

Figure 4:
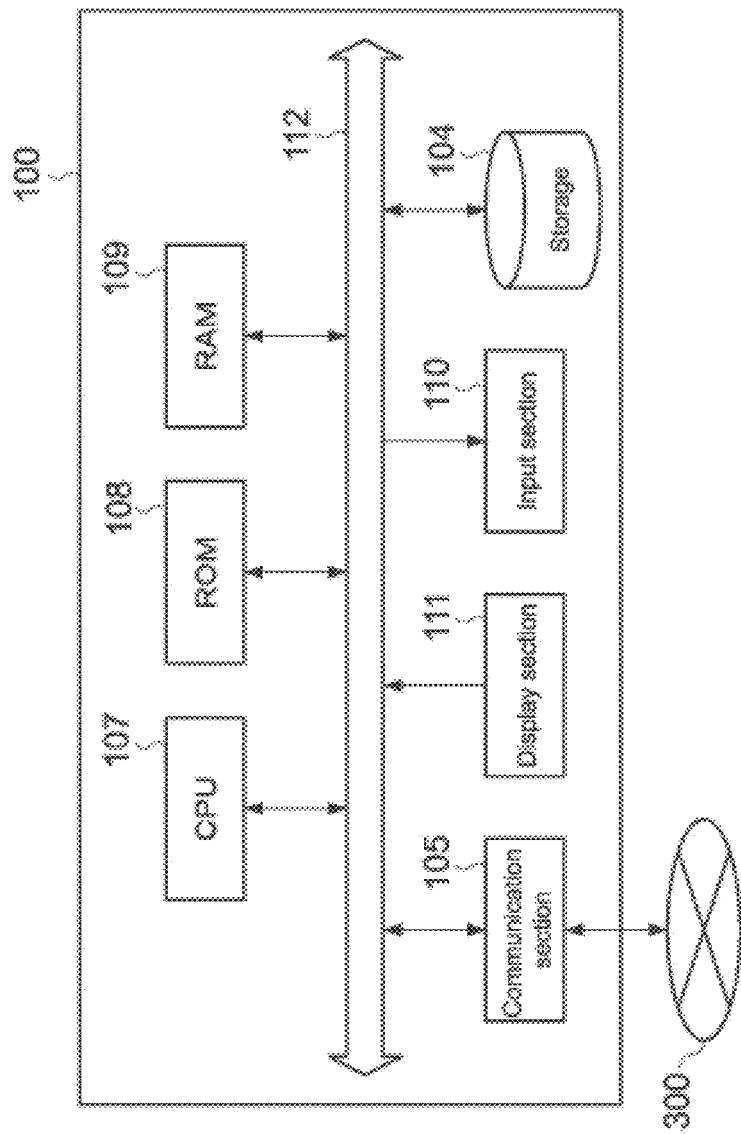
FIG. 4 is a block diagram showing a hardware configuration of an information terminal configuring the information processing system shown in FIG. 1.

FIG. 4 is a diagram showing a hardware configuration of the information terminal 100.

The hardware configuration of the information terminal 100 is similar to that of the medical information server apparatus 200 basically. That is, the information terminal 100 includes a CPU 107, a ROM 108, a RAM 109, a communication section 105, storage 104, an input section 110, a display section 111, and a system bus 112.

Here, the input section 110 and the display section 111 are the user interfaces described above.

In the ROM 108 or the storage 104, a program for software processing which the information terminal 100 should execute, and the like are stored. The CPU 107 loads an appropriate program from the ROM 108 or the storage 104 into the RAM 109 and performs calculation processing for an interpretation and execution in order to execute software processing which the information terminal 100 should execute. Accordingly, the CPU 107 causes a computer to function as the terminal information processing section 101, the browsing processing section 102, and the diagnostic information input section 103.

(Description of Operation)

Next, an operation of the information processing system 1 according to the embodiment of the present disclosure will be described.

Figure 5:
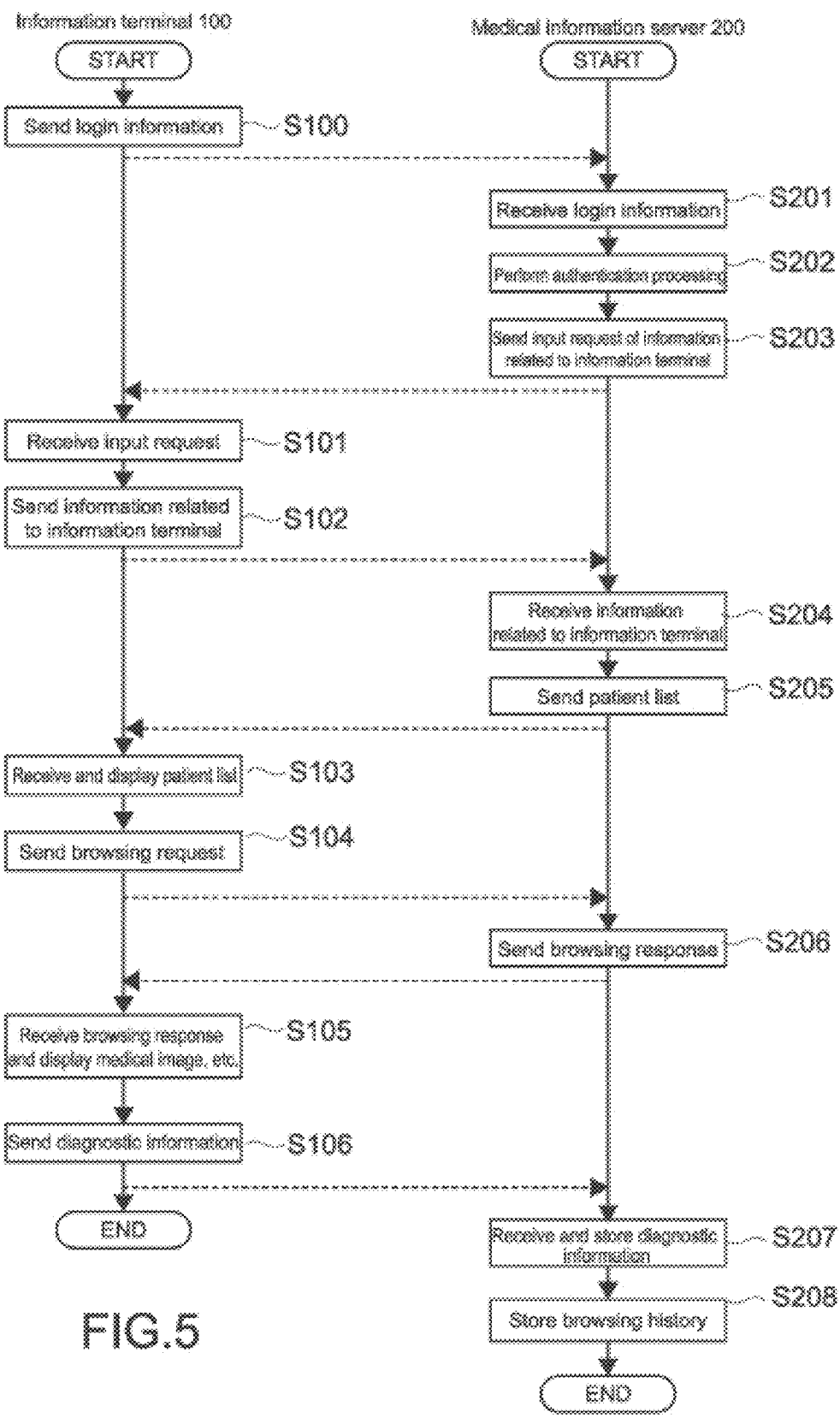
FIG. 5 is a sequence diagram showing a flow of processing between the information terminal and the medical information server in the information processing system according to the embodiment of the present disclosure.

FIG. 5 is a sequence diagram showing an operation of the first information terminal 100-1, the second information terminal 100-2, and the medical information server apparatus 200.

(1. Entire Operation)

When the information terminal 100 accesses the medical information server apparatus 200, the patient information management section 205 of the medical information server apparatus 200 takes out patient information from the storage 201 and sends it to the information terminal 100 as a patient list. The information terminal 100 sends a browsing request for a medical image related to a patient selected in the patient list received from the medical information server apparatus 200 as a diagnostic target to the medical information server apparatus 200. When receiving the browsing request from the information terminal 100, the medical information server apparatus 200 reads out a medical image from the storage 201 and sends it to the information terminal 100. The information terminal 100 shows the medical image received from the medical information server apparatus 200 to the user 5 by displaying it on the display section 111. The information terminal 100 accepts an input of a diagnostic result from the user 5 who browsed the medical image and sends the diagnostic result to the medical information server apparatus 200. The medical information server apparatus 200 stores the received diagnostic result in the diagnostic information table 211 of the storage 201.

(2. Login Processing)

As shown in FIG. 5, the information terminal 100 (the first information terminal 100-1 and the second information terminal 100-2) sends a login request which includes login information necessary for login such as the hospital ID and the password input by the user 5 from the input section 110 to the medical information server apparatus 200 (step S100). When receiving the login request from the information terminal 100 (step S201), the terminal information management section 203 of the medical information server apparatus 200 performs predetermined authentication processing based on the login information which is included in this login request (step S202). When the authentication is failed, the terminal information management section 203 sends an error to the information terminal 100. When the authentication succeeds, the terminal information management section 203 of the medical information server apparatus 200 sends an input request for information on the information terminal (step S203).

Here, a case where the information related to the information terminal of the first information terminal 100-1 has been registered in the medical information server apparatus 200 and the information related to the information terminal of the second information terminal 100-2 has not been registered in the medical information apparatus 200 is assumed.

(Login of Second Information Terminal 100-2)

When receiving the input request (step S101), the second information terminal 100-2 which has not been registered in the medical information server apparatus 200 takes out the terminal ID, the terminal nickname, the user interface specification information and the doctor ID that are the information related to the information terminal stored in the storage 104-2 and returns them to the medical information server apparatus 200 (step S102).

When receiving the information related to the information terminal from the second information terminal 100-2 (step S204), the terminal information management section 203 of the medical information server apparatus 200 registers these pieces of information in the terminal information table 209 newly. For example, in FIG. 12, information related to the information terminal with the terminal ID of 2 is added to the terminal information table 209. With this new registration of the information related to the information terminal, the terminal information management section 203 of the medical information server apparatus 200 sets a value of the diagnostic confirmation/temporal confirmation flag. The terminal information management section 203 may set the value of the diagnostic confirmation/temporal confirmation flag automatically based on the user interface specification information in the received information related to the information terminal, for example. Also, the value of the diagnostic confirmation/temporal confirmation flag may be determined so as to be "0" in a case of the new registration. At any rate, in this example, since the second information terminal 100-2 is assumed to be an information terminal with lower user interface specifications than the first information terminal 100-1, the value of the diagnostic confirmation/temporal confirmation flag is set as "0", that is, the authority to diagnose is set as "temporal diagnostic confirmation".

Accordingly, after that, the medical information server apparatus 200 recognizes the second information terminal 100-2 as a terminal which is granted an authority of "temporal diagnostic confirmation" and thus is capable of processing the diagnostic information from the second information terminal 100-2.

(Login of First Information Terminal 100-1)

In the following description, a case where the information related to the information terminal of the first information terminal 100-1 has been registered in the medical information sever apparatus 200 is assumed. It should be noted that, in this example, since the first information terminal 100-1 is assumed to be a terminal with higher user interface specifications than the second information terminal 100-2, the value of the diagnostic confirmation/temporal confirmation flag is set as "1", that is, the authority to diagnose is set as "diagnostic confirmation" in a case of the registration.

When receiving the input request for information related to the information terminal from the medical information server apparatus 200 (step S101), the first information terminal 100-1 which has been registered in the medical information server apparatus 200 takes out the terminal ID and the doctor ID which are stored in the storage 104-1 and returns them to the medical information server apparatus 200 (step S102).

When receiving the terminal ID and the doctor ID from the first information terminal 100-1 (step S204), the terminal information management section 205 of the medical information server apparatus 200 searches for the corresponding record (information related to the information terminal) from the terminal information table 209 based on the terminal ID and the doctor ID and confirms the value of the diagnostic confirmation/temporal confirmation flag in the record. Accordingly, the terminal information management section 205 determines that the authority to diagnose of the first information terminal 100-1 is "diagnostic confirmation".

Accordingly, after that, the medical information server apparatus 200 recognizes the first information terminal 100-1 as a terminal which is granted an authority of "diagnostic confirmation" and thus is capable of processing the diagnostic information from the first information terminal 100-1.

After the authority to diagnose granted to the information terminal 100 which has succeeded in login is determined, the patient information management section 205 of the medical information server apparatus 200 sends a patient list created based on the patient information which is stored in the storage 201 to the information terminal 100 (the first information terminal 100-1, the second information terminal 100-2) (step S205). The patient list is a list for a doctor to select a patient as a diagnostic target and is configured by information such as a patient ID, a patient name, a gender, a date of birth for each of the patients.

When receiving the patient list (step S103), the browsing processing section 102 of the information terminal 100 displays the patient list on the display section 111. The browsing processing section 102 of the information terminal 100 accepts the selection of the patient as a diagnostic target from the patient list by an input operation to the input section 110 by the user 5. The browsing processing section 102 of the information terminal 100 sends a browsing request for a medical image of the selected patient to the medical information server apparatus 200 (step S104). It should be noted that the browsing request for the medical image includes information such as a patient ID, screen resolution, a range or a position of an image to be browsed, and a zoom magnification.

When receiving the browsing request for the medical image from the information terminal 100, the image providing section 207 of the medical information server apparatus 200 confirms the authority to diagnose granted to the information terminal 100 by referring to the value of the diagnostic confirmation/temporal confirmation flag of the terminal information table 209. Further, the image providing section 207 takes out the medical image of the requested patient from the storage 201. Then, the image providing section 207 sends a browsing response including at least the confirmed information related to the authority to diagnose and the medical image to the information terminal 100 (step S206). When receiving the browsing response, the browsing processing section 102 of the information terminal 100 generates a browsing environment of the medical image to be displayed on the display section 111 based on the information related to the authority to diagnose, the medical image, and the like, which are included in the browsing response (step S105).

(3. Temporal Diagnostic Confirmation)

Figure 7:
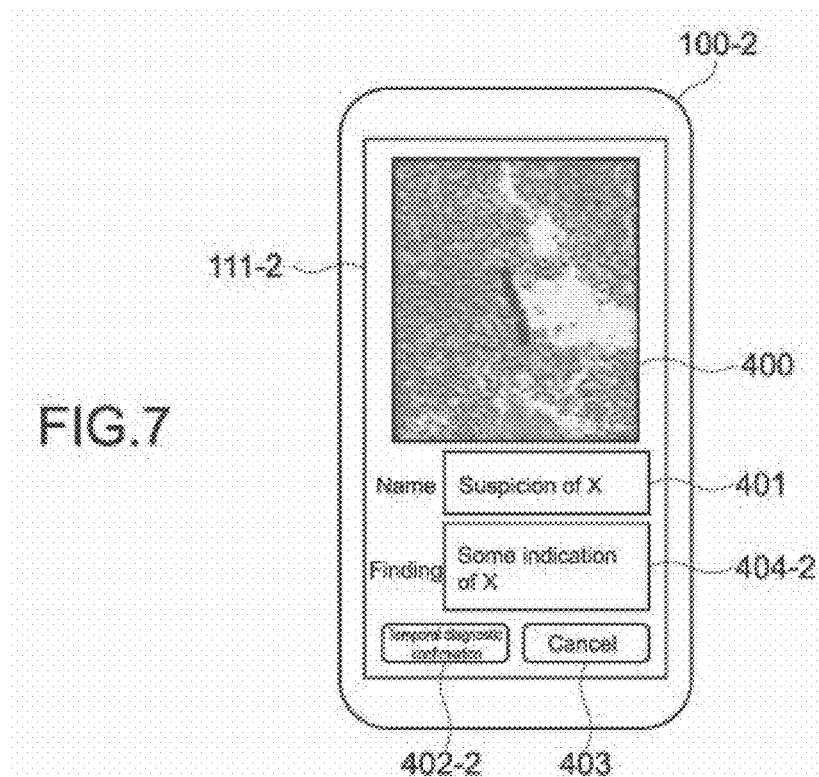

Next, a browsing environment of the medical image in the second information terminal 100-2 to which an authority of "temporal diagnostic confirmation" is granted will be described. FIG. 7 is a diagram showing the browsing environment of the medical image in the second information terminal 100-2.

The browsing processing section 102-2 of the second information terminal 100-2 displays a diagnosis target image 400, an entry field of a diagnosis 401, an entry field of a finding 404-2, a temporal diagnostic confirmation button 402-2, and a cancel button 403 on the display section 111-2. Here, the temporal diagnostic confirmation button 402-2 and the cancel button 403 are GUI elements generated due to that the authority information of "temporal diagnostic confirmation" is included in the browsing response.

It should be noted that, here, although the corresponding medical image of the patient is transferred from the medical information server apparatus 200 to the second information terminal 100-2, the patient information including the patient name, the patient ID, the gender, the age, and the like as well as the medical image may be transferred to the second information terminal 100-2 to be displayed on the display section 111-2.

Now, return to the description of the flowchart of FIG. 5. The doctor who is the user 5 performs a diagnosis with respect to the medical image displayed on the display section 111-2 and is capable of inputting the diagnosis into the entry field of a diagnosis 401 and inputting the finding into the entry field of a finding 404-2 by using the input section 110-2. When the doctor who is the user 5 operates the temporal diagnostic confirmation button 402-2, the diagnostic information input section 103-2 takes out the information input to the entry field of a diagnosis 401 and the entry field of a finding 404-2. Then, the diagnostic information input section 103-2 sends the information taken out from the entry field of a diagnosis 401 and the entry field of a finding 404-2 (the diagnosis, the finding) and the information such as the terminal ID, the doctor ID, the image ID, the position coordinates, the magnification, and the time and date as the diagnostic information to the medical information server apparatus 200 (step S106). Here, the position coordinates are absolute coordinates of the central position of the diagnosis target image 400 which is displayed on the display section 111-2 in the whole space of the medical image.

The diagnostic information management section 206 of the medical information server apparatus 200 assigns a diagnostic information ID to the diagnostic information received from the second information terminal 100-2 and registers it in the diagnostic information table 211 (step S207). At this time, the diagnostic information management section 206 confirms that the authority of "temporal diagnostic confirmation" is granted to the second information terminal 100-2 by referring to the diagnostic confirmation/temporal confirmation flag of the terminal information table 209, for example, and sets the value which represents that it is not diagnostic confirmation such as "0" to the diagnostic information table 211 as the information as to existence or non-existence of diagnostic confirmation.

Furthermore, the browsing history management section 204 registers the terminal ID, the doctor ID, the image ID, the position coordinates, the magnification, and the time and date which are received from the second information terminal 100-2 as new browsing history in the browsing history table 210 (step S208).

Moreover, even if the information has been input into the entry field of a diagnosis 401 and the entry field of a finding 404-2, the diagnostic information input section 103-2 of the second information terminal 100-2 considers the information invalid when detecting that the cancel button 403 has been operated, and sends the information such as the terminal ID, the doctor ID, the image ID, the position coordinates, the magnification, and the time and date as the browsing information to the medical information server apparatus 200. Accordingly, in the medical information server apparatus 200, only the registration of the browsing history in the browsing history table 210 by the browsing history management section 204 is performed.

Incidentally, the position or the zoom magnification of the diagnosis target image 400 to be displayed on the display section 111-2 of the second information terminal 100-2 in the whole space of the medical image can be changed arbitrarily by the operation of the user 5. The browsing processing section 102-2 of the second information terminal 100-2 calculates the position of the following diagnosis target image in response to the operation, generates a browsing request including the position information of the new diagnosis target image and sends it to the medical information server apparatus 200. The image providing section 207 of the medical information server apparatus 200 takes out the corresponding part of the medical image from the storage 201 in response to the browsing request including the position information of the new diagnosis target image. Then, the image providing section 207 sends the browsing response including the medical image to the second information terminal 100-2. As described above, the second information terminal 100-2 can repeat browsing for a diagnosis by moving the position of the diagnosis target image in the whole space of the medical image. With this, the information such as the terminal ID, the doctor ID, the image ID, the position coordinates, the magnification, and the time and date is stored as browsing history in the browsing history table 210 one after another.

(4. Diagnostic Confirmation)

In this information processing system 1, the diagnostic information which is acquired from the second information terminal 100-2 as well as the diagnosis target image can be displayed on the first information terminal 100-1. The doctor who is the user 5 can determine "diagnostic confirmation" by checking the diagnostic information and the diagnosis target image and by correcting the diagnostic information as necessary, using the first information terminal 100-1.

Figure 6:
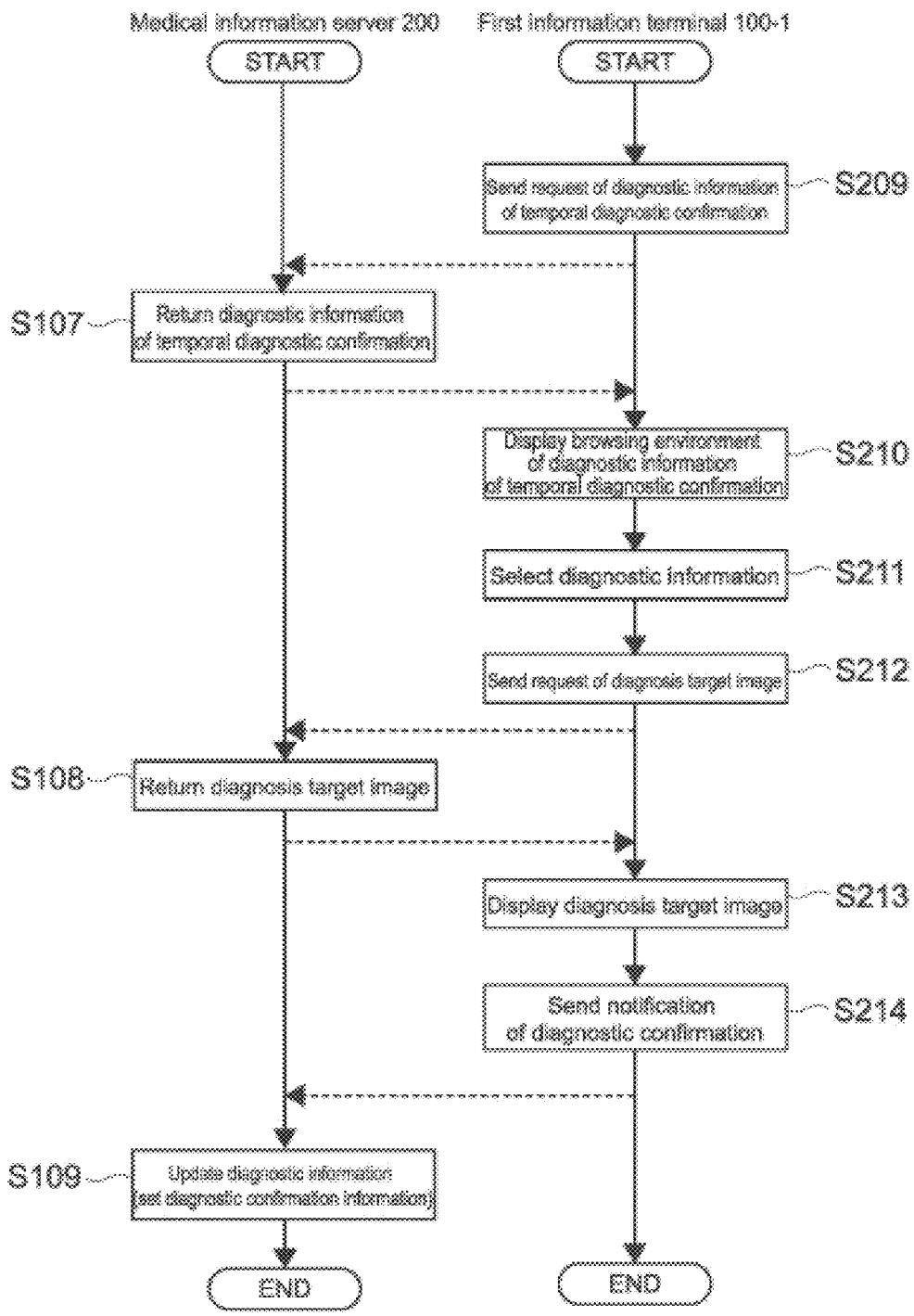
FIG. 6 is a sequence diagram showing a flow of processing between a first information terminal and the medical information server in the information processing system according to the embodiment of the present disclosure.

FIG. 6 is a flowchart related to processing of the diagnostic confirmation.

When receiving an instruction for starting processing of diagnostic confirmation from a user, the browsing processing 102-1 of the first information terminal 100-1 sends an acquiring request for the diagnostic information of the temporal diagnostic confirmation to the medical information server apparatus 200 (step S209).

The diagnostic information management section 206 of the medical information server apparatus 200 takes out the diagnostic information, in which the value showing that it is not diagnostic confirmation is set, as the information as to existence or non-existence of diagnostic confirmation from the medical information table 211 as the diagnostic information of the temporal diagnostic confirmation when receiving the acquiring request. Then, the diagnostic information management section 206 returns the diagnostic information of the temporal diagnostic confirmation to the first information terminal 100-1 (step S107).

When acquiring the diagnostic information of the temporal diagnostic confirmation and the image including the diagnosis target image, the browsing processing section 102-1 of the first information terminal 100-1 generates a browsing environment of the diagnostic information of the temporal diagnostic confirmation to be displayed on the display section 111-1 based on the acquired information (step S210).

Figure 8:
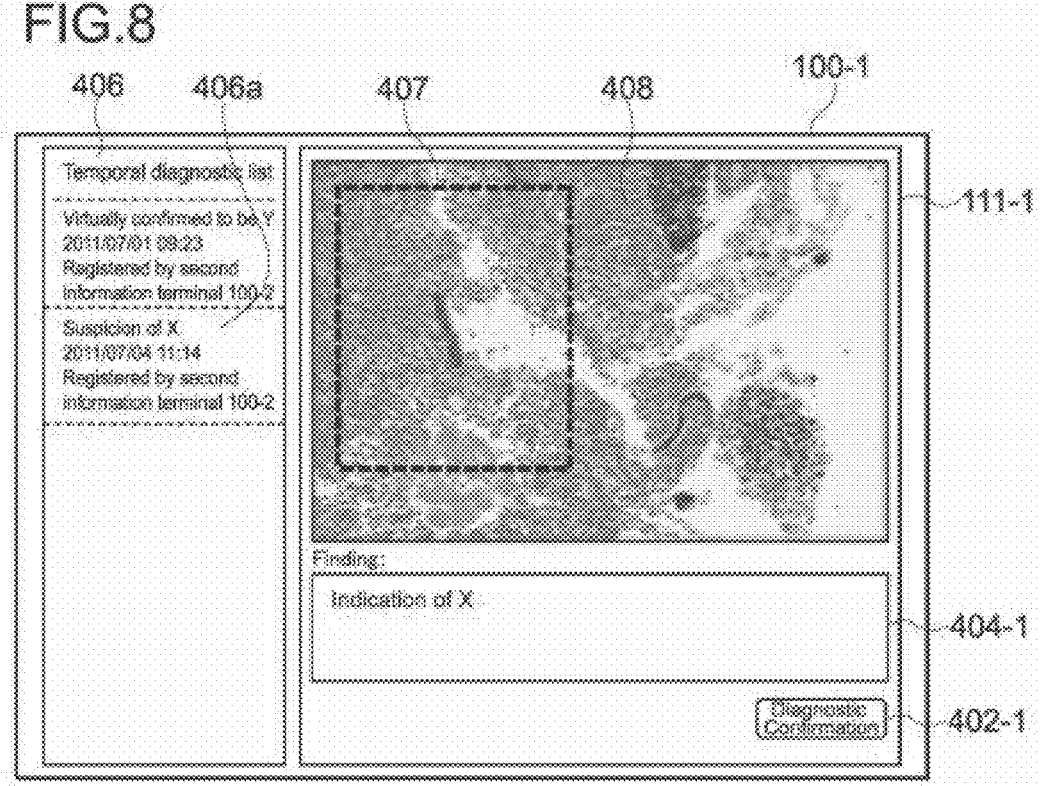

FIG. 8 is a diagram showing the browsing environment of the diagnostic information of the temporal diagnostic confirmation. The browsing environment of the diagnostic information of the temporal diagnostic confirmation is configured by a temporal diagnostic list 406, an image display area 408, a finding reference area 404-1, a diagnostic confirmation button 402-1, and the like. The temporal diagnostic list 406 is created from the diagnosis, the terminal ID, the doctor ID, and the like, which are included in the diagnostic information of the temporal diagnostic confirmation. In the finding reference area 404-1, the information on the finding which is included in the acquired diagnostic information is displayed.

When the user 5 selects diagnostic information in the temporal diagnostic list 406 (step S211), the browsing processing section 102-1 sends an acquiring request for an diagnosis target image corresponding to the diagnostic information to the medical information server apparatus 200 (step S212). Here, the acquiring request for a diagnosis target image includes a diagnostic information ID, information on resolution of the image display area 408, and the like.

When receiving the acquiring request for an diagnosis target image, the image providing section 207 of the medical information server apparatus 200 refers to the information such as the image ID, the position information, the magnification, and the like of the corresponding diagnostic information from the diagnostic information table 211 based on the diagnostic information ID which is included in the acquiring request. The image providing section 207 specifies the corresponding diagnosis target image based on the referenced information, takes out an image which corresponds to the resolution of the image display area 408 including the diagnosis target image from the electronic medical record 208 and returns it to the first information terminal 100-1 (step S108).

When obtaining the image which corresponds to the resolution of the image display area 408 including the diagnosis target image, the browsing processing section 102-1 of the first information terminal 100-1 displays the image on the image display area 408 of the display section 111-1 (step S213). At this time, the browsing processing section 102-1 calculates the position of the diagnosis target image in the image displayed in the image display area 408 and overlays a frame border 407 surrounding the position on the image displayed on the image display area 408 for displaying.

When obtaining a new finding by the diagnosis in the first information terminal 100-1, the doctor who is the user 5 can input the new finding into the finding reference area 404-1 using the input section 110-1.

When the diagnosis is completed, the user 5 operates the diagnostic confirmation button 402-1. When detecting that the diagnostic confirmation button 402-1 has been operated, the browsing processing section 102-1 of the first information terminal 100-1 sends a notification of the diagnostic confirmation including the diagnostic information ID to the medical information server apparatus 200 (step S214). At this time, in a case where there is updated information of a finding, the new information of a finding is also sent to the medical information server apparatus 200.

When receiving the notification of the diagnostic confirmation including the diagnostic information ID from the first information terminal 100-1, the diagnostic information management section 206 of the medical information server apparatus 200 determines the corresponding diagnostic information which has been registered in the diagnostic information table 211, based on the diagnostic information ID, and updates the information as to existence or non-existence of diagnostic confirmation to the value which represents the diagnostic confirmation such as "1" (step S109).

It should be noted that, in the flowchart of FIG. 6, although the first information terminal 100-1 obtains the image including the diagnosis target image which corresponds to the diagnostic information selected by the user after acquiring the diagnostic information of the temporal diagnostic confirmation, the diagnostic information and the image including the diagnosis target image may be obtained simultaneously.

(5. Display of Browsing History)

When receiving an instruction for displaying browsing history of an arbitrary medical image from the doctor who is the user 5, the first information terminal 100-1 sends an acquiring request for browsing history of the arbitrary medical image to the medical information server apparatus 200.

When receiving the acquiring request for browsing history of the arbitrary medical image from the first information terminal 100-1, the browsing history management section 204 of the medical information server apparatus 200 takes out all the browsing history related to the corresponding medical image (image ID) and sends it to the first information terminal 100-1 from the browsing history table 210.

Figure 9:
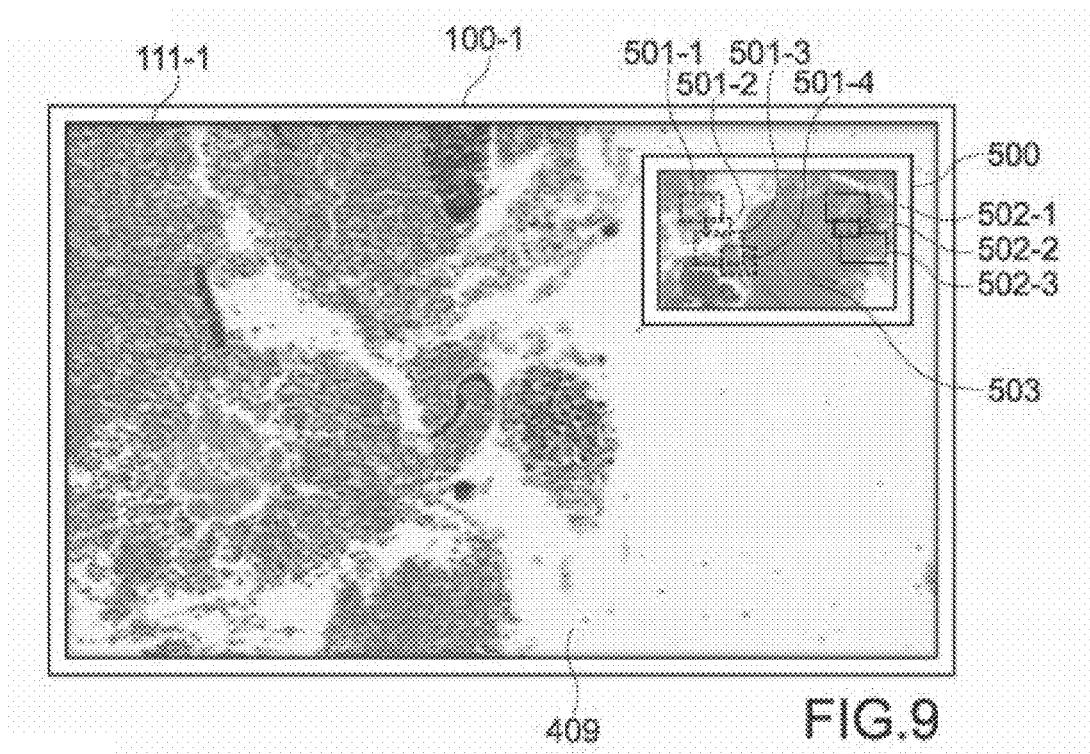

When acquiring the browsing history from the medical information server apparatus 200, the browsing processing section 102-1 of the first information terminal 100-1 calculates the browsing completion position in the whole space of the medical image based on the position coordinates and the magnification of each of the browsing history. When obtaining the calculation result of each browsing completion position, the browsing processing section 102-1 displays the browsing completion position on the display section 111-1 in a state where it can be identified for each of the information terminals in the whole space of the medical image. Accordingly, as shown in FIG. 9, for example, the user 5 can confirm how the browsing of the medical image is performed by each information terminal 100. FIG. 9 is an example of displaying the browsing history by two information terminals 100. In this example, browsing completion positions 501-1 to 501-4 by one information terminal 100 and browsing completion positions 502-1 to 502-3 by the other information terminal 100 can be identified by a difference of, for example, a line type (e.g., color, pattern, thickness).

As another method of displaying the browsing completion positions for each of the information terminals so as to be identified, a method using a difference of painting (e.g., depth of painting or color) can also be considered. An overlapping part due to a plurality of times of browsing may reflect the number of overlapping in the depth of painting or color. Accordingly, the user can instinctively know the area of image in which browsing is performed intensively.

(6. Movie Display of Browsing History)

In the information processing system 1 according to the embodiment of the present disclosure, the browsing history can also be displayed dynamically by switching the browsing completion position by the information terminal in an order of a time and date which is included in a series of browsing history information for display.

Figure 10:
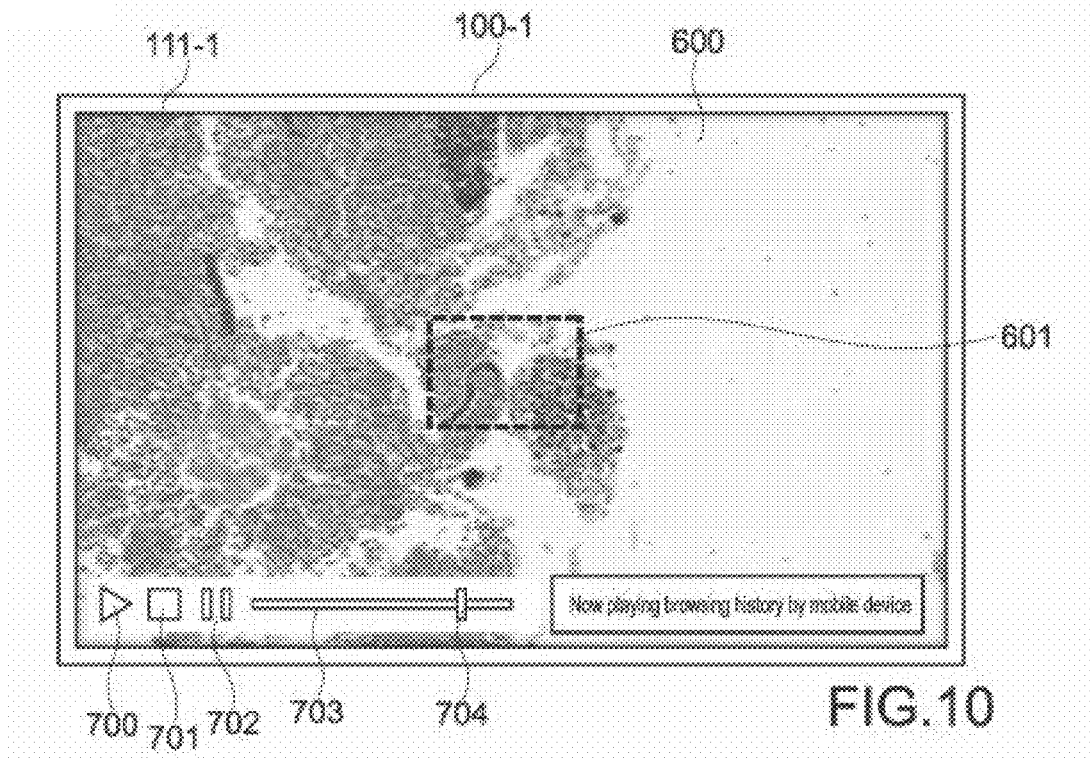
FIG. 10 is a diagram showing the first information terminal shown in FIG. 1 and shows a state displaying browsing history.

FIG. 10 is a diagram showing a dynamic display environment of the browsing history. The dynamic display environment of the browsing history includes a whole medical image 600, a reproduction button 700, a stop button 701, a pause button 702, a seek bar 703, and a frame border 601. The reproduction button 700 accepts an input according to the display of the browsing history from the user. The frame border 601 represents the browsing completion position.

When detecting that the reproduction button 700 has been operated, the browsing processing section 102-1 of the first information terminal 100-1 dynamically switches the frame border 601 which represents the browsing completion position on the displayed medical image 600 for displaying based on the series of browsing history of the designated information terminal 100, which is obtained from the medical information server apparatus 200. The dynamic switching display of the frame border 601 is finished by the operation of the stop button 701. When the pause button 702 is operated, the browsing processing section 102-1 stops the dynamic switching display of the frame border 601 and maintains the display state of the frame border 601 at the time of the operation. In the seek bar 703, a time between the time of the first browsing and the time of the last browsing in the series of browsing history is assigned. A movable part 704 of the seek bar 703 moves along with the switching display of the browsing history. Further, the movable part 704 can be moved by the manual operation of the user. Then, the display position of the browsing history is also moved along with the operation to move the movable part 704. Accordingly, the user can select the display position of the browsing history arbitrarily.

(7. Method of Registering Information Terminal)

Next, a method of registering the information terminal 100 to the medical information server apparatus 200 will be described.

Figure 11:
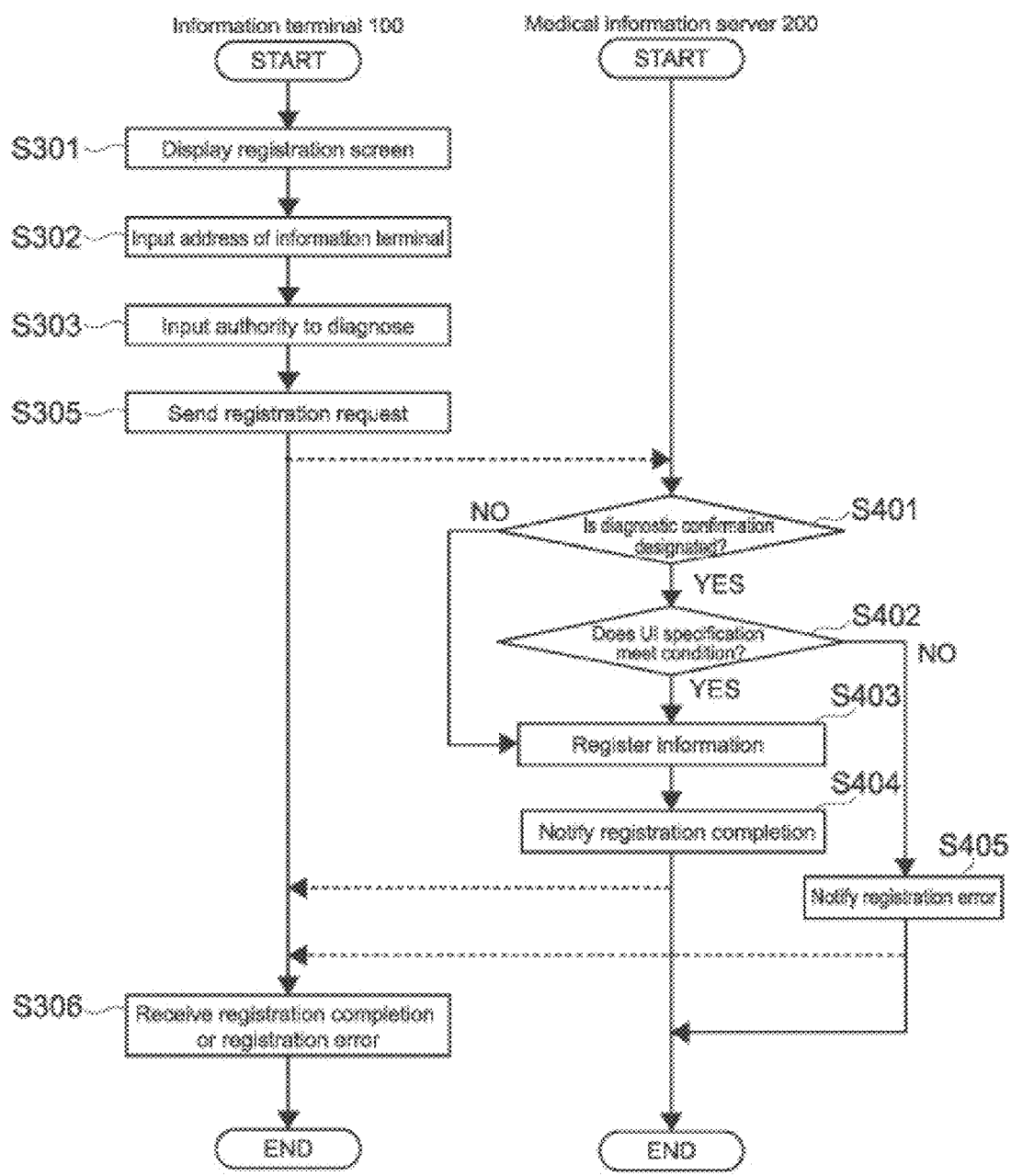
FIG. 11 is a sequence diagram showing a flow of registration processing of the information terminal in the information processing system according to the embodiment of the present disclosure.

FIG. 11 is a sequence diagram showing a flow of registration processing of an information terminal in the information processing system 1 according to the embodiment of the present disclosure.

When receiving an instruction for displaying a registration screen from the user 5, the terminal information processing section 101 of the information terminal 100 displays a terminal registration screen (not shown) which is used for registering an information terminal on the display section 111 (step S301).

The terminal ID, the doctor ID, the terminal nickname, the user interface specification information (e.g., the screen size and the screen resolution of the display section, and the type of the input section) which are information related to the information terminal registered in the storage 104 are displayed on the terminal registration screen. Also, an input item of the address of the medical information server apparatus 200, a selection item of an authority to diagnose, a terminal registration button, and the like are provided on the terminal registration screen as other input items of the terminal registration information.

The terminal information processing section 101 of the information terminal 100 accepts an input such as an IP (Internet Protocol) address or FQDN (Fully Qualified Domain Name) of the medical information server apparatus 200 into the input item of an address from the user (step S302).

Next, the terminal information processing section 101 of the information terminal 100 accepts an input of a selection into the selection item of an authority to diagnose from the user (step S303).

When the information which is used for the registration is insufficient due to a failure of extracting the user interface specification information from the storage 104 or the like on the terminal registration screen, the terminal information processing section 101 of the information terminal 100 accepts a manual input of information by the user and compensates the insufficient information.

After that, when detecting that the terminal registration button has been operated by the user 5, the terminal information processing section 101 of the information terminal 100 sends a registration request including the information related to the information terminal and the information related to the authority to diagnose to the medical information server apparatus 200 (step S305).

The terminal information management section 203 of the medical information server apparatus 200 confirms the information of the authority to diagnose which is included in the registration request acquired from the information terminal 100 (step S401). When the authority to diagnose is designated as "temporal diagnostic confirmation" (NO in step S401), the terminal information management section 203 registers the information such as the terminal ID, the doctor ID, the nickname, and the user interface specification information, which are the information related to the information terminal included in the registration request, in the terminal information table 209 and sets "0" as the value of the diagnostic confirmation/temporal confirmation flag (step S403). After that, the terminal information management section 203 notifies the information terminal 100 of the registration completion of the information terminal 100 (step S404).

When the authority to diagnose is designated as "diagnostic confirmation" (YES in step S401), the terminal information management section 203 determines whether the user interface specifications of the information terminal 100 meet a certain condition based on the user interface specification information in the acquired terminal registration information (step S402). When the user interface specifications of the information terminal 100 meet the certain condition (YES in step S402), the terminal information management section 203 registers the information such as the terminal ID, the doctor ID, the nickname, and the user interface specification information in the terminal registration information in the terminal information table 209 and sets "1" as the value of the diagnostic confirmation/temporal confirmation flag (step S403). After that, the terminal information management section 203 notifies the information terminal 100 of the registration completion of the information terminal 100 (step S404).

When the user interface specifications of the information terminal 100 do not meet the certain condition (NO in step S402), the terminal information management section 203 notifies the information terminal 100 of a registration error of the information terminal 100 (step S405).

When receiving the notification of the registration completion (step S306), the information terminal 100 finishes the registration processing.

On the other hand, when receiving the notification of the registration error (step S306), the information terminal 100 returns to step S301 and displays the terminal registration screen. It thus becomes possible to start over the registration.

It should be noted that, in the setting of the authority to diagnose in the registration processing of the information terminal, an authority of either "diagnostic confirmation" or "temporal diagnostic confirmation" is granted based on the user interface specifications of the information terminal. However, an authority of either "diagnostic confirmation" or "temporal diagnostic confirmation" may be granted based on the user selection, regardless of the user interface specifications.

As described above, in this embodiment, an authority of either "diagnostic confirmation" or "temporal diagnostic confirmation" is granted to each of the information terminals 100 based on the user interface specifications or the like. A diagnostic result by the information terminal 100 to which the authority of "temporal diagnostic confirmation" is granted (the second information terminal 100-2) is treated as the diagnostic information of the temporal diagnostic confirmation. On the other hand, the information terminal 100 to which the authority of "diagnostic confirmation" is granted (the first information terminal 100-1) can change the attribution of the diagnostic result from "temporal diagnostic confirmation" to "diagnostic confirmation" by performing a formal diagnosis on the diagnostic information of temporal diagnostic confirmation by the second information terminal 100-2 again.

As described above, since a plurality of the information terminals 100 each of which has a different authority to diagnose can be used to diagnose, various types of information terminals 100 each of which has different user interface specifications, such as a mobile terminal and a desktop personal computer, can be used to diagnose. Accordingly, it is possible to perform a diagnosis more frequently. Further, it is also possible to improve the quality of a diagnosis because it is difficult to obtain a formal diagnostic result by the information terminal 100 with relatively low user interface specifications, such as a mobile terminal. In other words, it is possible to improve a diagnosis in both quality and efficiency by the information processing system 1 according to this embodiment.

<Modified Example>

In an information terminal which meets a condition to which the authority of "diagnostic confirmation" is granted under the user interface specifications, the user may change the authority to diagnose from "diagnostic confirmation" to "temporal diagnostic confirmation" or from "temporal diagnostic confirmation" to "diagnostic confirmation" as appropriate by the information terminal, for example, even after the value of the diagnostic confirmation/temporal confirmation flag is temporarily set.

Alternatively, an authority to diagnose is not determined uniquely based on the user interface specifications, the medical information server apparatus may supply a message which recommends an authority to be granted to the information terminal to the information terminal, and a final authority may be set based on an instruction by the user of the information terminal.

Furthermore, regardless of the user interface specifications, the authority to diagnose may be set based on the instruction by the user of the information terminal.

The present disclosure can employ the following configurations.

In an embodiment, a medical information server is provided. The medical information server includes a medical information unit configured to determine a diagnose authority to an information terminal thereby allowing a diagnosis by the information terminal to be identified by the diagnose authority.

In an embodiment, the medical information unit is further configured to register information associated with the information terminal, and wherein the information is utilized to determine the diagnose authority.

In an embodiment, the information includes user interface specification information associated with the information terminal.

In an embodiment, the medical information unit is further configured to allow displaying of medical information based on determining the diagnose authority.

In an embodiment, the medical information includes a medical image.

In an embodiment, the medical information unit is further configured to allow displaying of an input configured to allow input of the diagnosis based on the diagnose authority.

In an embodiment, the medical information unit is further configured to allow displaying of a diagnosis history associated with the diagnosis.

In an embodiment, the medical information unit is further configured to allow displaying of a browsing history associated with the diagnosis history.

In an embodiment, the medical information unit is further configured to allow displaying of a dynamic display environment associated with the browsing history.

In another embodiment, an information terminal is provided. The information terminal includes an information terminal unit configured to provide information that allows a determination of a diagnose authority thereby allowing a diagnosis by the information terminal to be identified by the diagnose authority.

In an embodiment, the information includes user interface specification information associated with the information terminal.

In an embodiment, the information terminal unit is further configured to display medical information based on determining the diagnose authority.

In an embodiment, the medical information includes a medical image.

In an embodiment, the information terminal unit is further configured to display an input configured to allow input of the diagnosis based on the diagnose authority.

In an embodiment, the information terminal unit is further configured to display a diagnosis history associated with the diagnosis.

In an embodiment, the information terminal unit is further configured to display a browsing history associated with the diagnosis history.

In an embodiment, the information terminal is further configured to display a dynamic display environment associated with the browsing history.

In yet another embodiment, a diagnostic information processing system is provided.

The diagnostic processing system includes a medical information server comprising a medical server unit configured to determine a diagnose authority; and an information terminal comprising an information terminal unit configured to provide information to the server, wherein the diagnose authority is determined to the information terminal based on the information thereby allowing a diagnosis by the information terminal to be identified by the diagnose authority.

In an embodiment, the information includes user interface specification information associated with the information terminal.

In an embodiment, the medical information unit is further configured to allow displaying of medical information by the information terminal based on determining the diagnose authority.

In an embodiment, the medical information includes a medical image.

In an embodiment, the medical information unit is further configured to allow displaying of an input by the information terminal, and wherein the input is configured to allow input of the diagnosis based on the diagnose authority.

In an embodiment, the medical information unit is further configured to allow displaying of a diagnosis history associated with the diagnosis by the information terminal.

In an embodiment, the medical information unit is further configured to allow displaying of a browsing history associated with the diagnosis history by the information terminal.

In an embodiment, the medical information unit is further configured to allow displaying of a dynamic display environment associated with the browsing history by the information terminal.

In yet a further embodiment, the following are provided:

(1) An information processing apparatus, including
a terminal information management section configured to manage information on an authority to diagnose each medical image of a plurality of information terminals;
an image providing section configured to return a corresponding medical image, in response to a request for browsing the medical image from any one of the plurality of information terminals, to the information terminal; and
a diagnostic information management section configured to differentiate and manage a diagnostic result obtained from the information terminal with respect to the medical image provided to the information terminal based on information on an authority to diagnose of the information terminal.

(2) The information processing apparatus according to (1), in which
the diagnostic information management section differentiates and manages a diagnostic result provided from a first information terminal that is an information terminal being granted an authority to diagnose a medical image as a first confirmed diagnostic result, and a diagnostic result provided from a second information terminal that is an information terminal not being granted the authority to diagnose the medical image as a second confirmed diagnostic result.

(3) The information processing apparatus according to (2), in which
the diagnostic information management section returns the second confirmed diagnostic result and an diagnosis target image corresponding to the second confirmed diagnostic result in response to a request from the first information terminal.

(4) The information processing apparatus according to any one of (1) to (3), further including
a browsing history management section configured to manage browsing history of the medical image of each of the plurality of information terminals and return the browsing history in response to a request from the information terminal.

(5) The information processing apparatus according to any one of (1) to (4), in which the terminal information management section sets an authority to diagnose the medical image of the information terminal based on a specification of a user interface of the information terminal.

(6) An information processing method, including
managing, by a terminal information management section, information on an authority to diagnose each medical image of a plurality of information terminals;
returning, by an image providing section, a corresponding medical image, in response to a request for browsing the medical image from any one of the plurality of information terminals, to the information terminal; and
differentiating and managing, by a diagnostic information management section, a diagnostic result obtained from the information terminal with respect to the medical image provided to the information terminal based on information on an authority to diagnose of the information terminal.

(7) A program causing a computer to function as:
a terminal information management section configured to manage information on an authority to diagnose each medical image of a plurality of information terminals;
an image providing section configured to return a corresponding medical image, in response to a request for browsing the medical image from any one of the plurality of information terminals, to the information terminal; and
a diagnostic information management section configured to differentiate and manage a diagnostic result obtained from the information terminal with respect to the medical image provided to the information terminal based on information on the authority to diagnose the information terminal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 100-1 First information terminal
100-2 Second information terminal
110-1, 110-2 Input section
111-1, 111-2 Display section
200 Medical information server apparatus
201 Storage
203 Terminal information management section
204 Browsing history management section
206 Diagnostic information management section
207 Image providing section

The invention claimed is:

1. A medical information server comprising:
   circuitry configured to:
   receive a first identification information, which includes a first user identification and a first terminal identification, and a first request to access a first medical image from a first terminal device,
   judge a first diagnosis authority based on the first identification information as having a temporary diagnosis authority,
   transmit the first medical image to the first terminal device,
   receive first diagnostic information from the first terminal device,
   store the first diagnostic information as temporary diagnosis information associated with the first medical image,
   receive a second identification information, which includes a second user identification and a second terminal identification, and a second request to access a second medical image from a second terminal device,
   judge a second diagnosis authority based on the second identification information as having a definite diagnosis authority,
   transmit the temporary diagnosis information associated with the first medical image to the second terminal device,
   receive second diagnostic information from the second terminal device, and
   store the second diagnostic information as definite diagnosis information associated with the first medical image.

2. The medical information server of claim 1, wherein the circuitry is further configured to register information associated with the first terminal device, and wherein the registered information is utilized to determine the diagnosis authority.

3. The medical information server of claim 2, wherein the registered information includes user interface specification information associated with the first terminal device.

4. The medical information server of claim 1, wherein the circuitry is further configured to control displaying of medical information based on judging the diagnosis authority.

5. The medical information server of claim 4, wherein the medical information includes the first medical image.

6. The medical information server of claim 5, wherein the circuitry is further configured to control displaying of an input configured to allow input of the first diagnostic information based on the diagnose authority.

7. The medical information server of claim 6, wherein the circuitry is further configured to control displaying of a diagnosis history.

8. The medical information server of claim 7, wherein the circuitry is further configured to control displaying of a browsing history associated with the diagnosis history.

9. The medical information server of claim 8, wherein the circuitry is further configured to control displaying of a dynamic display environment associated with the browsing history.

10. The medical information server of claim 1, wherein the first user identification is the same as the second user identification.

11. A medical information processing method comprising:
    receiving a first identification information, which includes a first user identification and a first terminal identification, and a first request to access a first medical image from a first terminal device,
    judging a first diagnosis authority based on the first identification information as having a temporary diagnosis authority,
    transmitting the first medical image to the first terminal device,
    receiving first diagnostic information from the first terminal device,
    storing the first diagnostic information as temporary diagnosis information associated with the first medical image,
    receiving a second identification information, which includes a second user identification and a second terminal identification, and a second request to access a second medical image from a second terminal device,
    judging a second diagnosis authority based on the second identification information as having a definite diagnosis authority,
    transmitting the temporary diagnosis information associated with the first medical image to the second terminal device,
    receiving first diagnostic information from the second terminal device, and
    storing the second diagnostic information as definite diagnosis information associated with the first medical image.

12. A computer readable medium storing instructions, which when executed, cause a medical information server to:
    receive a first identification information, which includes a first user identification and a first terminal identification, and a first request to access a first medical image from a first terminal device,
    judge a first diagnosis authority based on the first identification information as having a temporary diagnosis authority,
    transmit the first medical image to the first terminal device,
    receive first diagnostic information from the first terminal device,
    store the first diagnostic information as temporary diagnosis information associated with the first medical image, receive a second identification information, which includes a second user identification and a second terminal identification, and a second request to access a second medical image from a second terminal device, judge a second diagnosis authority based on the second identification information as having a definite diagnosis authority, transmit the temporary diagnosis information associated with the first medical image to the second terminal device, receive second diagnostic information from the second terminal device, and store the second diagnostic information as definite diagnosis information associated with the first medical image.

* * * * *